United States Patent [19]

Smith

[11] Patent Number: 5,345,701

[45] Date of Patent: Sep. 13, 1994

[54] ADJUSTABLE ORTHOTIC

[76] Inventor: Leland R. Smith, 363 Dolphin Isle, Foster City, Calif. 94404

[21] Appl. No.: 95,355

[22] Filed: Jul. 21, 1993

Related U.S. Application Data

[63] Continuation of Ser. No. 804,423, Dec. 10, 1991, abandoned, which is a continuation-in-part of Ser. No. 692,316, Apr. 26, 1991, abandoned.

[51] Int. Cl.$^5$ .................................................. A61F 5/00
[52] U.S. Cl. .......................................... 36/144; 36/127; 36/140
[58] Field of Search ............... 36/144, 148, 140, 155, 36/159–163, 172, 174, 110, 112, 127, 132, 136, 1, 8.1, 11.5, 25 R, 106; 273/187 B

[56] References Cited

U.S. PATENT DOCUMENTS

| | | | |
|---|---|---|---|
| 1,958,097 | 5/1934 | Shaw | 36/43 X |
| 2,631,387 | 3/1953 | Shaw | 36/43 X |
| 2,847,769 | 8/1958 | Schlesinger | 36/127 |
| 2,855,704 | 10/1958 | Schlesinger | 36/127 |
| 2,959,873 | 11/1960 | Schlesinger | 36/127 |
| 2,959,874 | 11/1960 | Schlesinger | 36/127 X |
| 3,337,972 | 8/1967 | Stollman et al. | 36/1 X |
| 3,982,336 | 9/1976 | Herro | 36/25 R |
| 4,073,075 | 2/1978 | O'Brien | 36/136 X |
| 4,081,918 | 4/1978 | O'Brien | 36/127 X |
| 4,085,758 | 4/1978 | Castiglia | |
| 4,333,247 | 6/1982 | Marinelli | 36/11.5 |
| 4,333,472 | 6/1982 | Tager | |
| 4,510,700 | 4/1985 | Brown | |
| 4,603,698 | 8/1986 | Cherniak | |
| 4,620,376 | 11/1986 | Talarico, II | 36/25 R X |
| 4,685,227 | 8/1987 | Simmons | 36/25 R X |
| 4,694,590 | 9/1987 | Greenwalt | |
| 4,715,131 | 12/1987 | Kremendahl | |
| 4,742,625 | 5/1988 | Syder et al. | 36/11.5 X |
| 4,803,747 | 2/1989 | Brown | |
| 4,841,648 | 6/1989 | Shaffer | |
| 4,937,985 | 7/1990 | Boraventure | 36/132 |
| 4,945,659 | 8/1990 | DeMarchi et al. | 36/132 X |

FOREIGN PATENT DOCUMENTS

| | | | |
|---|---|---|---|
| 149093 | 3/1937 | Austria | 36/76 |
| 163940 | of 1921 | United Kingdom | 36/163 |

Primary Examiner—Richard J. Apley
Assistant Examiner—Linda C. M. Dvorak
Attorney, Agent, or Firm—James E. Eakin; Janet K. Castaneda

[57] ABSTRACT

An orthopedic device for adjustable correction of varus and valgus conditions includes an orthotic having at least one attachment device thereon together with a plurality of mating posts having varying degrees of correction for forefoot and rearfoot attachment. In some instances the orthotic is formed as part of a shoe.

14 Claims, 8 Drawing Sheets

ADJUSTABLE ORTHOTIC

This application is a continuation of Ser. No. 07/804,423 filed Dec. 10 1991, now abandoned, which is a continuation-in-part of Ser. No. 07/692,316 filed Apr. 26, 1991, now abandoned.

FIELD OF THE INVENTION

This application relates to methods for forming orthopedic devices for use with shoes and other footwear, and to methods for forming such orthopedic devices.

BACKGROUND OF THE INVENTION

Orthopedic devices for the feet (hereinafter sometimes called "orthotics") are well known, and have been used by laypersons and podiatrists for many years. Orthotics of this type range from a simple arch support to a custom formed support for the foot. It has been estimated that 50% of the population could benefit from some form of shoe orthopedic device to improve support and balance for the foot.

Since the feet are the foundation on which the rest of the body is supported, foot misalignment can result in many forms of discomfort for the patient. Symptoms which have been known to develop from such misalignment are plantar fasciitis, hammertoes, bunions, achilles tendonitis, and others. Misalignment can also cause or exacerbate knee, hip or back problems.

In an ideal situation, orthotics can cure two forms of misalignment. First, the orthotic should match the sole of the foot to the ground and, second, the orthotic should bring the remainder of the body into proper alignment with the foot. It will be appreciated that the feet, legs and upper body represent a closed kinetic chain in which a change at any one point can affect the remaining points. Obtaining proper alignment of the foot with the ground can be simplified to "bringing the ground up to meet the foot", while obtaining proper alignment of the foot with the rest of the body involves adjusting the relative position of the foot to the legs.

Many pre-formed orthotics are available to remedy a variety of patient maladies relating to posture, stance and gait. Most such pre-formed orthotics are formed of a polymeric material and sold in a variety of sizes and shapes, with the expectation that one or another of the pre-cast shapes will be close enough to the patient's needs that the orthotic will be acceptable.

However, in most such instances, the fit—and thus the amount of improvement—provided by the mass produced orthotic is far less than perfect. Typical problems involve the conformity of the orthotic to the sole of the foot, which affects the uniformity of support, as well as the amount of correction provided. Since only a few sizes of mass produced orthotics can be justified from an economic standpoint, this requires the patient to accept a significant amount of compromise in comfort and fit, and leads many patients to abandon use of the pre-formed orthotic.

Custom fitted orthotics are also available, but typically are very expensive. In the conventional approach, a custom orthotic is constructed by starting with a complete cast of the foot. Such custom orthotics are frequently, though not always, done under the supervision of a podiatrist. The impression which results from the casting is then sent to a laboratory where the custom formed orthotic is developed from the impression. As a result, the custom orthotic typically conforms to the sole of the patient's foot much better than a mass produced orthotic. Such custom orthotics, however, have two serious limitations. While the fit is much better in most instances, if an error is made either in making the initial casting, or making the orthotic from the casting, the resulting orthotic is substantially useless. Second, and often more important, changes in the patient's physiology require that the custom orthotic be recast. This latter limitation with the existing art can also affect patients using mass produced orthotics, and is particularly applicable to children. Children typically outgrow custom inlays in approximately one year. Given the expense of such custom orthotics, the economic burden can become substantial for either type of recasting.

SUMMARY OF THE INVENTION

The present invention overcomes many of the limitations of the prior art, and provides nearly all of the benefits of custom orthotics, while at the same time permitting adjustment of the orthotic after initial construction.

The present invention provides a fully custom, adjustable orthotic specially fitted to the patient, yet capable of being adjusted to ensure continued proper fit and support.

In particular, a pre-existing footsole portion of an orthotic formed of polyethylene terephthalate or other acceptable polymer has included in the bottom thereof an attachment device. One or more posts or wedges, which may vary in configuration and amount of correction, includes on the top thereof an attachment device capable of mating with the attachment device on the underside of the footsole portion. When attached, the post and footsole become substantially an integrated orthotic.

In many instances, only the ball of the foot needs adjustment. However, in some instances, both the foreward portion of the foot and the heel need alignment correction. In such instances, the orthotic of the present invention can include multiple attachment devices to permit correction of alignment at both locations.

The attachment device may use any of a variety of techniques, including but not limited to interlocking dimples, Velcro ™, bolts, interlocking geometries and dowels. The primary requirement of such attachment devices is that they remain firmly attached under the stress of walking and running, including remaining attached during the flexing of the orthotic which occurs with such activities.

By replacing one wedge with others having different correction factors, such as different wedge angles, an adjustable orthotic is provided which can be specially fitted to the patient. As a result, improved fit and support can be provided. For convenience, different colors may be used for different correction factors.

In addition, in the event the patient's physiology changes, the orthotic of the present invention can be modified readily to provide continued excellent support, thus substantially reducing the economic burden associated with both custom and mass produced orthotics. This can be particularly helpful for children. Additionally, the lower cost of the present device will make correction of gait problems in children much more accessible to a significant segment of the population.

Still further, the adjustable orthotic of the present invention may be configured as part of the sole of an otherwise conventional shoe. In such an arrangement, the sole of the shoe may be specially configured to permit detachable forefoot and heel portions to be added and adjusted in a manner otherwise similar to the orthotic.

There has therefore been a need for an orthotic which can be adjusted readily by a podiatrist to provide a substantially custom correction of a patient problem.

In addition, there has been a need for an orthotic which can be readily modified by altering the amount of correction.

Still further, there has been a need for an orthotic which can be readily altered by removing a first wedge and substituting therefor an alternative wedge such as might be necessary to provide a different amount of correction.

Yet further, there has been a need for an orthotic which can be integrated into the sole of an otherwise substantially conventional shoe.

These and other objects of the invention will be better understood from the following Detailed Description of the Invention, taken together with the appended Figures.

The Figures

FIGS. 6A-D shows an alternative implementation for attaching a post to an orthotic which has been found especially useful in many situations.

Figure 7A:
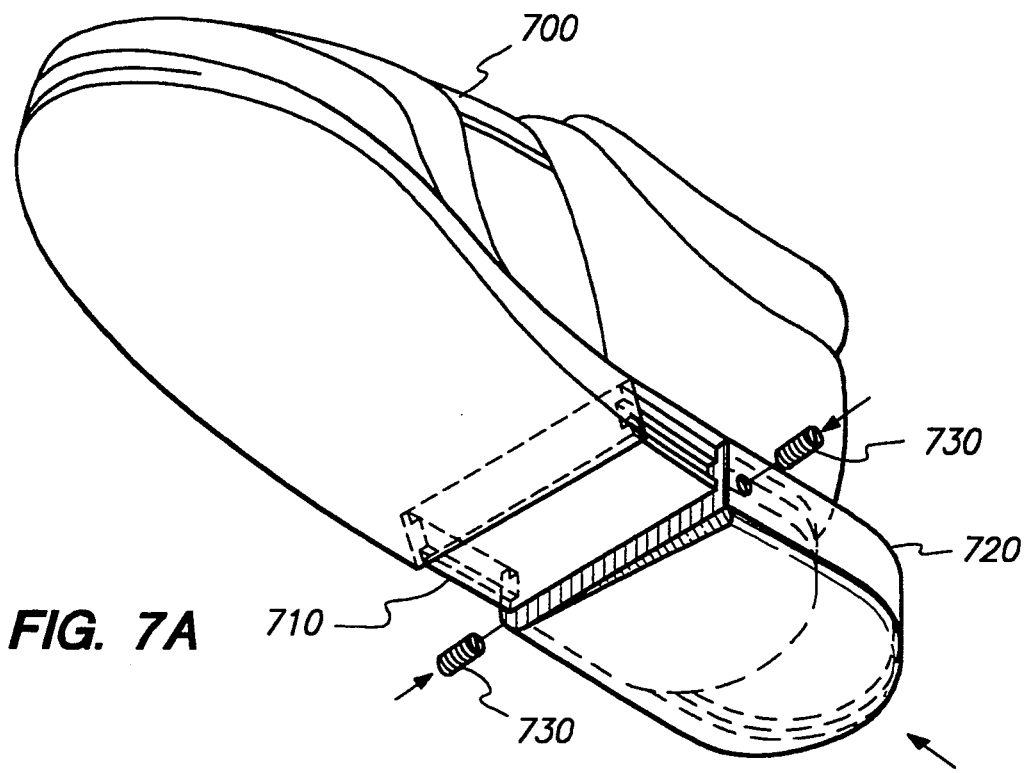
Figure 7B:
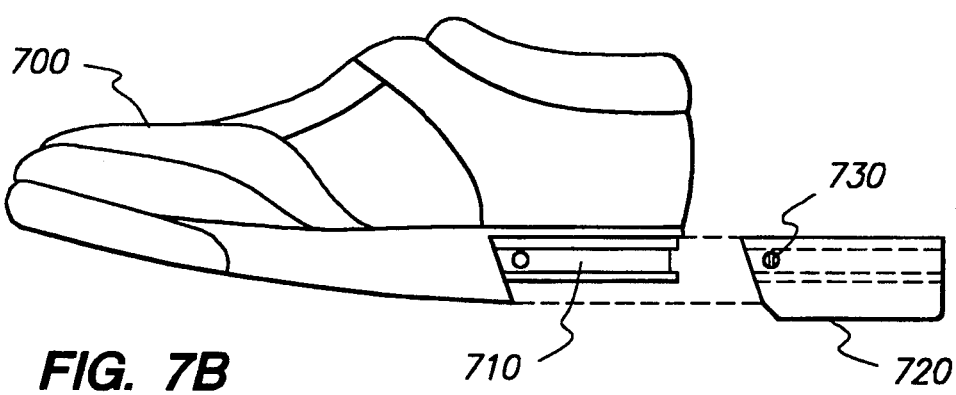

FIGS. 7A-B show an alternative method of attaching posts to an orthotic.

Figure 8A:
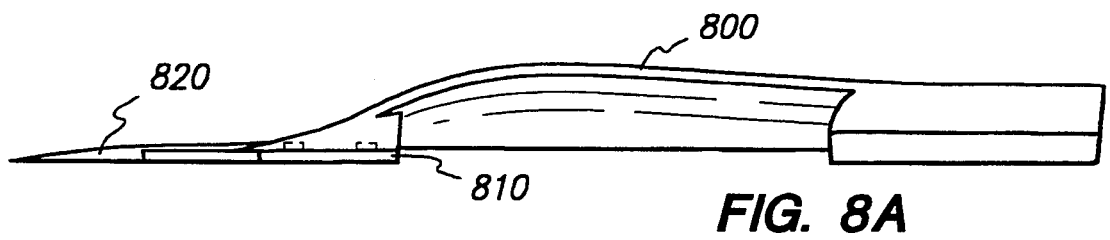
Figure 8B:
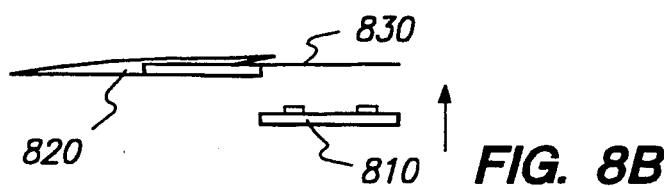

FIGS. 8A-B show an orthotic having a toe extension.

FIGS. 9A-E show methods of attaching a post involving bolts or rods.

Figure 10:
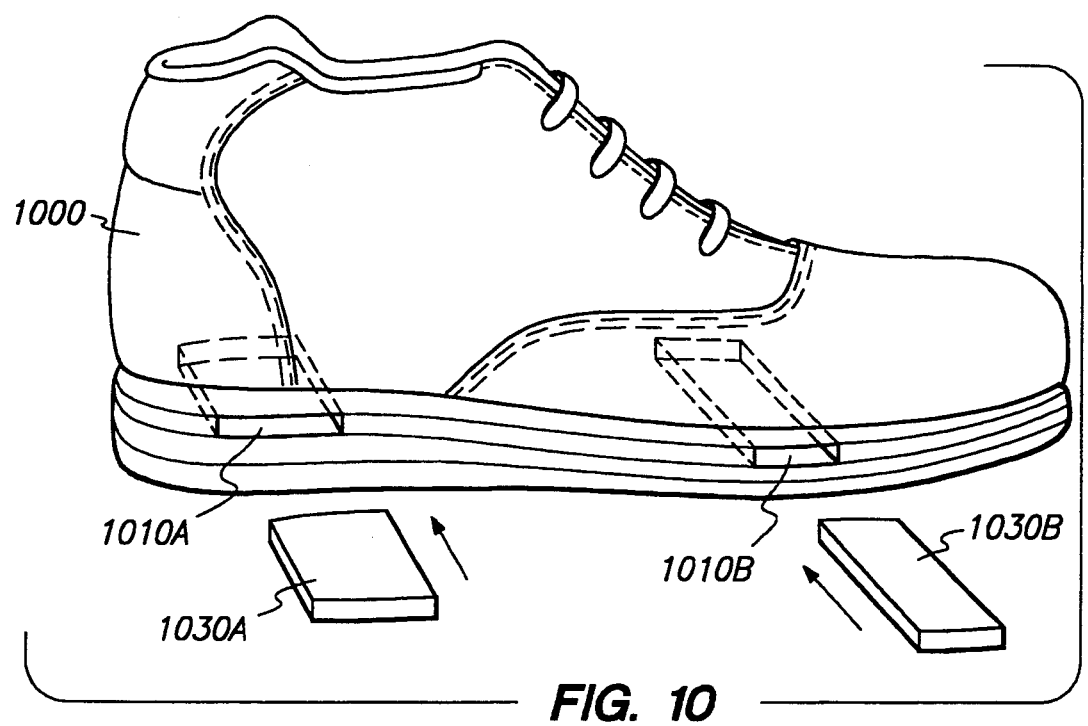

FIG. 10 shows a shoe having posts affixed by side insertion.

DETAILED DESCRIPTION OF THE INVENTION

Figure 1:
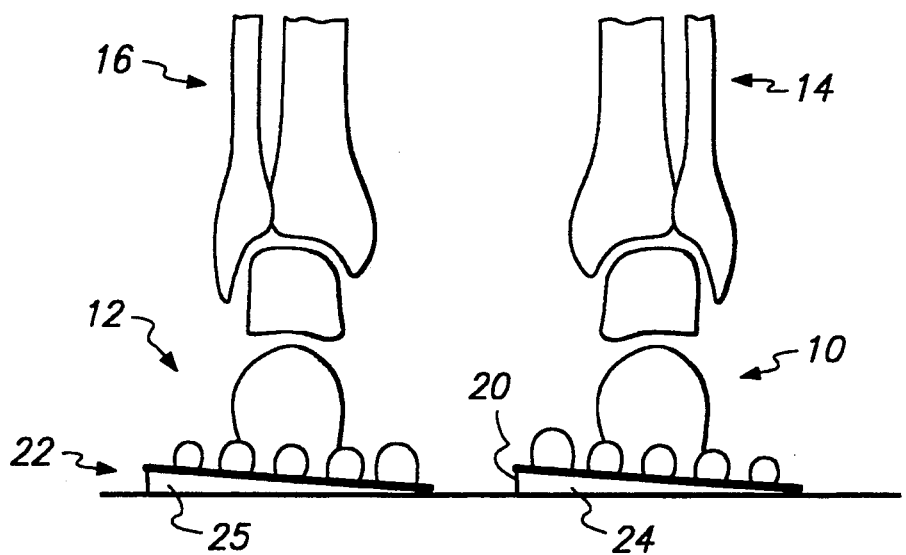
FIG. 1 is a generalized front elevational view of the lower extremities of a patient in need of alignment correction, including an orthotic according to the present invention.
Figure 5:
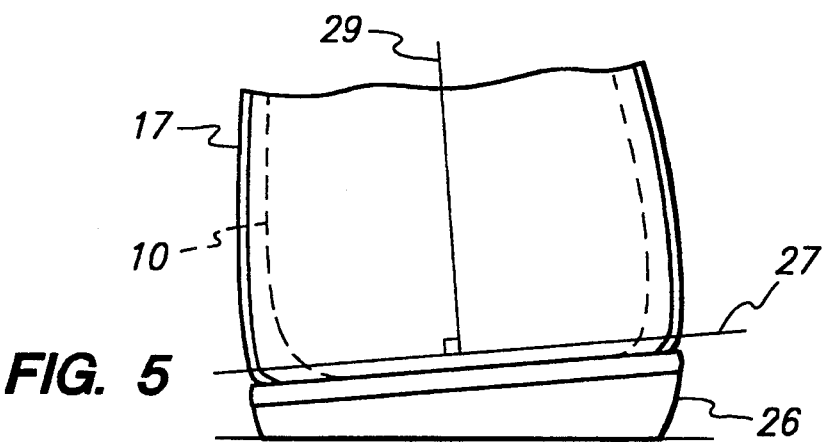
FIG. 5 shows from rear elevational view one example of the alignment correction available with the adjustable orthotic of the present invention.

Referring first to FIG. 1, the generalized bone structure of the lower extremities of a patient 5 can be seen in front elevational view together with an orthotic according to the present invention. Two feet 10 and 12 support respective legs 14 and 16. As can be seen from FIG. 1, the feet can be seen to need correction of alignment relative to the ground and to the remainder of the body. In particular, the right foot 10 is shown in valgus, while the left foot is shown in varus. A pair of orthotic devices, indicated generally at 20 and 22, for left and right feet, respectively, can be seen below the respective feet, with rear foot and forefoot posts or wedges 24 and 26 in place for adjustment of the foot alignment and lower extremity alignment. Those skilled in the art will recognize from FIG. 1 that the orthotic of the present invention is intended to be capable of treating both varus and valgus misalignment. With reference to FIG. 5, one example of the type of alignment correction available with the present invention can be seen. A foot 10, shown in dashed line form within the shoe 17, requires correction. By adding the wedge 26, the plane of the ground is raised to meet the sole of the foot 10, as shown by the line 27. This in turn causes the alignment of the foot 10 to change as shown by the line 29. It will be appreciated that the capability of adding a rear wedge 26 also provides the possibility of adding a heel lift for independent adjustment of heel height.

Figure 2A:
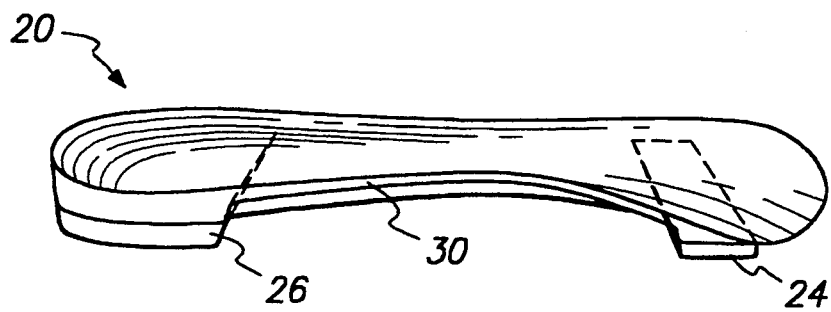
FIG. 2a shows a typical orthotic according to the present invention in perspective side view, including front and back correcting wedges.
Figure 2B:
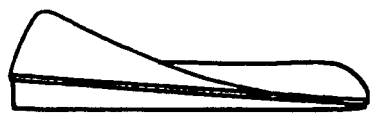
FIG. 2b shows the orthotic of FIG. 2a in front elevational view.
Figure 2C:
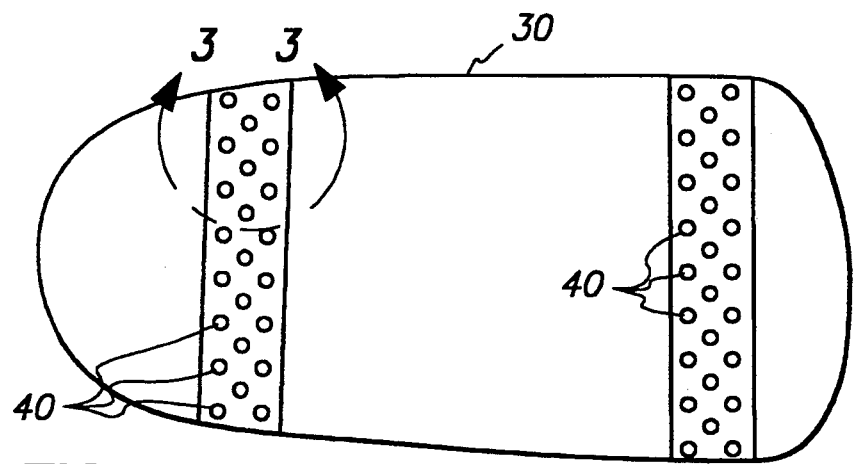
FIG. 2c shows the orthotic of FIG. 2a in bottom view with the correcting wedges removed.

With reference now to FIGS. 2a-2c, the orthotic device 20, which for purposes of example only is an orthotic device for the right foot, includes a footsole portion 30 together with the pair of correcting wedges 24 and 26. The wedges 24 and 26 can be seen (FIG. 2b) to change the angle of the bottom of the footsole portion 30 relative to the ground, thus bringing the ground up to meet the soles of the patient's foot. It will be appreciated that the wedges 24 and 26 can be formed at any angle, depending on the patient's needs. Likewise, it will be appreciated by those skilled in the art that the orientation of the wedges 24 or 26 can change depending upon whether valgus or varus correction is required. In at least some instances it may be desirable to provide an indicia for readily differentiating wedges of different angles, such as by making wedges of different correction factor in different colors.

Figure 3:
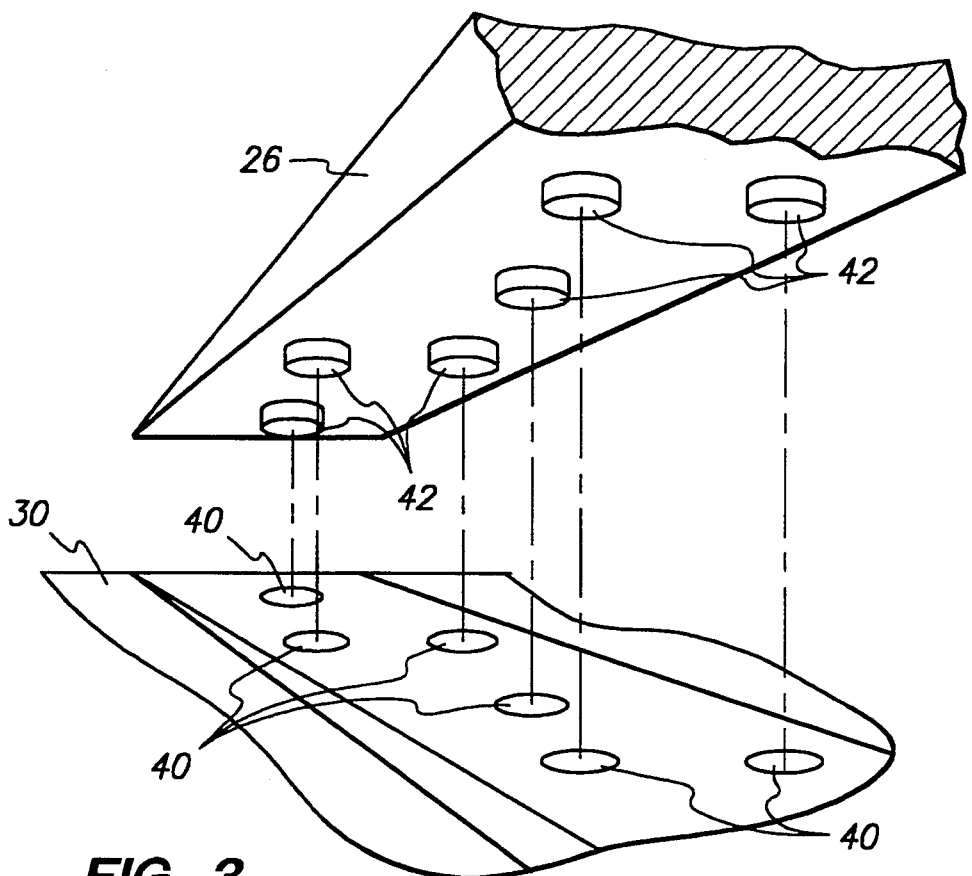
FIG. 3 shows in detail an attachment portion of an orthotic according to the present invention.

Referring particularly to FIGS. 2c and 3, a preferred type of attachment device is shown in detail. The bottom of the footsole portion 30 can be seen to have formed therein a pattern of recesses 40, which in the exemplary embodiment shown here are circular but may in other embodiments be of any acceptable form factor. The top portion of the posts or wedges 24 and 26 can also be seen to have a pattern of raised members 42 mated to the pattern of recesses 40, such that the wedges 24 or 26 can be affixed to the footsole portion 30 and will mechanically adhere thereto through the stress of walking, running or other ambulatory movement, while at the same time being readily removable when required for adjustment or other treatment.

Although a pattern of mating recessed and raised members is presently preferred as a method of affixing the wedges 24 or 26 to the footsole 30, other approaches are also acceptable. For example, Velcro ™ and the related class of "hook-and-loop" fasteners are acceptable attachment devices in at least some instances, as are T-slot connectors or any other device which provides a firm mechanical attachment which will withstand the stresses of walking or similar activities. Alternatively, orthotic posts could be inserted under the insole of a shoe into recesses in the upper portion of the sole of the shoe.

The footsole portion 30 may comprise any of a number of materials, and can be formed by casting, extrusion, or other molding processes. A variety of materials are acceptable, including nylon, polystyrene, high density polyethylene, and numerous other polymers, but the presently preferred material is cast polyethylene terephthalate. For at least some applications, it is preferable for the polyethylene terephthalate to be fiber filled, although fiber content is not necessary in all cases.

The footsole portion 30 may be either preformed or custom molded, depending on the needs of the patient and the economic issues associated with custom molding. In addition, in some embodiments it may also be desirable to make the raised members 42 out of different, more rigid material which may be embedded either in the footsole portion 30 or the orthotic attachments or wedges 24 and 26. Such an arrangement may, depending upon the environment and the materials used for the footsole portion 30 and attachments 24 and 26, provide better retention of the orthotic to the footsole.

Figure 4:
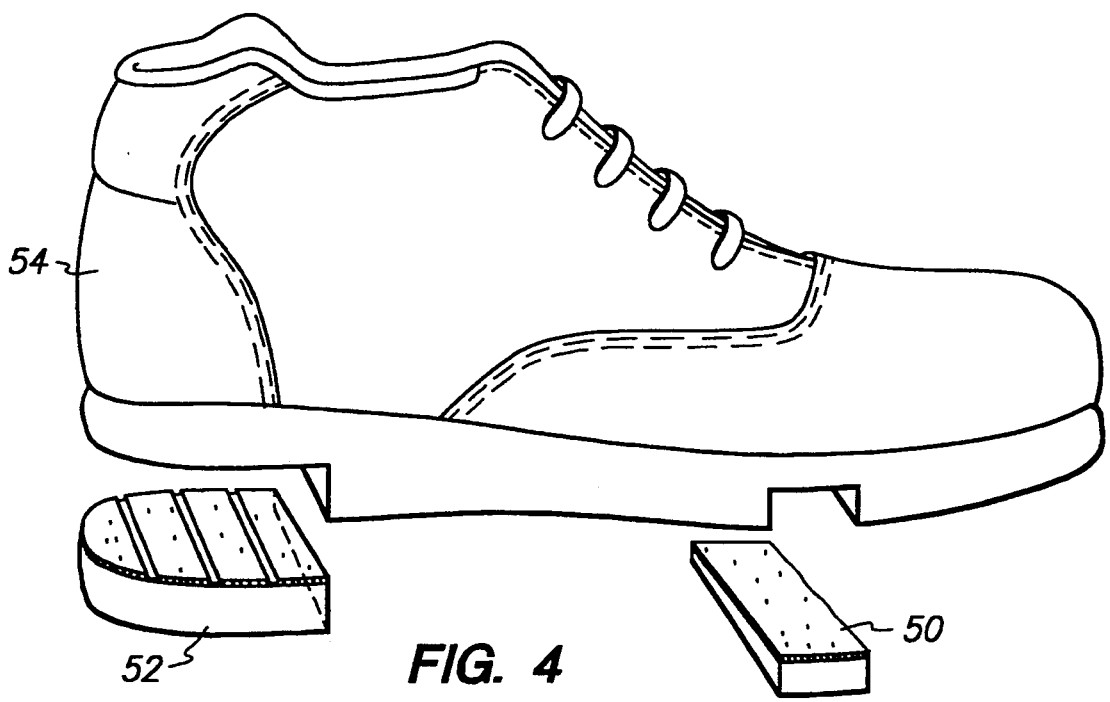
FIG. 4 shows the orthotic attachments of the present invention incorporated into the sole of an otherwise conventional shoe.

Referring next to FIG. 4, in some embodiments it may be desirable to integrate orthotic attachments 50 and 52 into the sole of a shoe 54, in which case the footsole portion may be separated from the wedges. Although the shoe of FIG. 4 shows Velcro TM as a means of attachment for purposes of example, the presently preferred method of attachment is the mating raised members and recesses discussed above in connection with FIG. 3.

While in many instances it will be desirable to use the same material for the posts as for the footsole, in some instances it may be desirable to vary the materials for the respective portions. For example, improved shock absorption may be provided by using posts of a hard rubber combined with footsole constructed of a thermoplastic material. The easy replacement of the posts also provides an easy method for minimizing normal wear and tear, particularly on the shoe of FIG. 3, in that a worn post can simply be removed and a replacement snapped into place.

Additionally, it is possible to provide an adjustable arch support in accordance with the present invention simply by providing a removable arch attachment and providing mating attachment members to a removable arch attachment and to the appropriate portion of the footsole portion 30.

By combining the footsole portion 30 with the adjustable wedges 24 and 26, a completely adjustable, substantially custom fitted orthotic may be provided without the cost or delay normally associated with custom orthotics, while at the same time providing a highly effective method for optimizing balance and support for the patient.

Figure 6A:
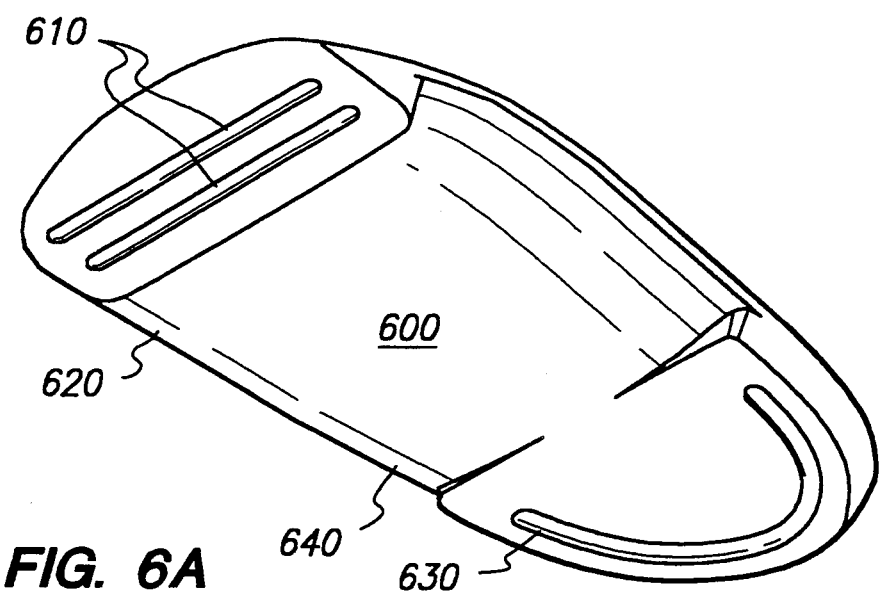
Figure 6B:
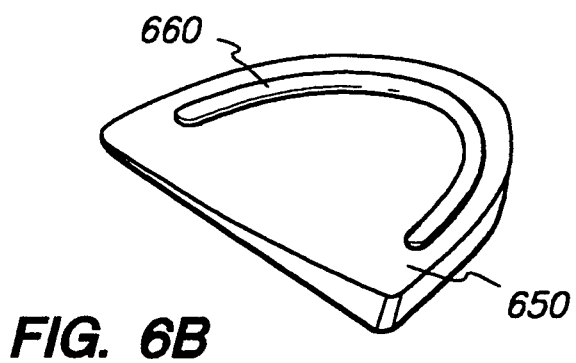
Figure 6C:
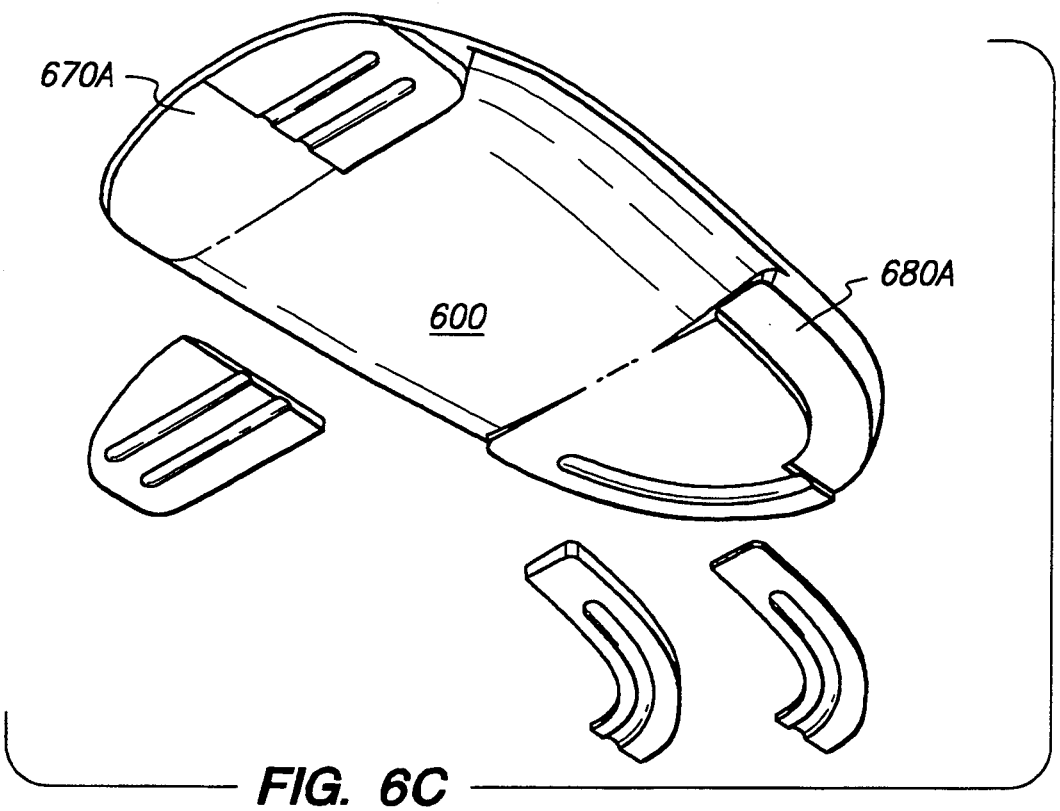
Figure 6D:
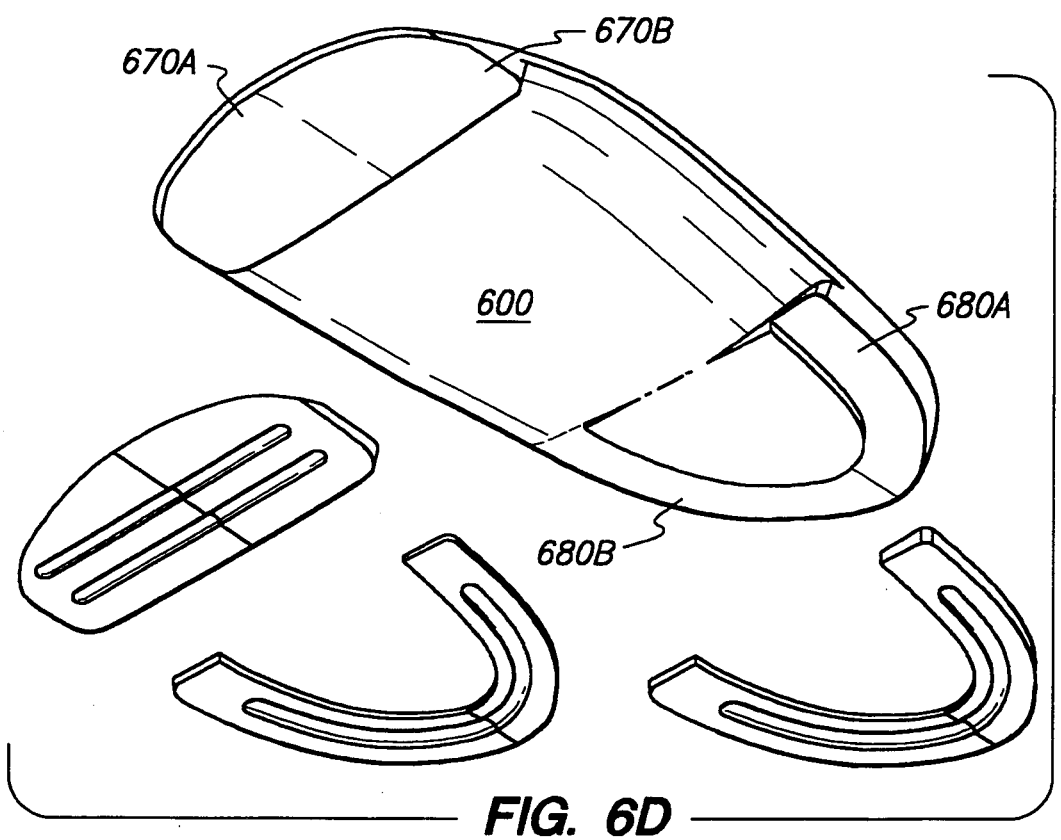

An alternative method of attaching posts to an orthotic can be appreciated from FIGS. 6A–6D, in which the bottom of an orthotic 600 is shown in FIG. 6A. Integrally formed into the orthotic 600 are forefoot grooves 610 at the forefoot portion 620 and rearfoot grooves 630 at the ankle portion 640 of the orthotic 600. One or more such grooves may be provided at each portion, as illustrated in the single rearfoot groove and the double forefoot grooves. A mating rearfoot post 650 shown in FIG. 6B, having a ridge 660 formed thereon, connects to the orthotic 600 at the ankle or rearfoot portion 640 thereof by interlocking the ridge 660 into the groove 630. Alternatively, in some instances it is possible that the ridges could be placed on the orthotic and the grooves on the post. As can be appreciated from FIG. 6C, a forefoot post 670A can be provided to mate to the orthotic 600 in a similar manner. The approach of FIG. 6C also illustrates that a post need not extend across the entire sole of the orthotic, but instead may extend only part way. Additionally, and as best illustrated in FIGS. 6C and 6D, a plurality of partial posts may be provided for attachment next to one another, as shown by posts 670A-B and 680A-B. In addition, an arch wedge 690 may be provided if desired.

Referring next to FIG. 7, still a further arrangement for affixing a heel post to an otherwise conventional shoe can be seen. A shoe 700 includes at the heel thereof a mounting portion 710. A heel post 720, which forms substantially the entire heel of the shoe, slides over the mounting portion 710 and is locked into place with one or more fasteners 730, such as screws, dowels or other similar devices. As with other embodiments described above, this approach permits easy replacement of an entire heel, whether as the result of wear or adjustment of the angle of the heel post. Although not shown in this particular drawing, a front post can also be included if desired.

Referring next to FIGS. 8A–B, an orthotic having a toe extension according to the present invention can be better appreciated. It will be appreciated by those skilled in the art that in some cases support for the toes is required, and yet conventional, customized orthotics are too rigid to permit them to extend into the toe area because of the required flexing of the orthotic at the junction of the toes to the remainder of the foot. In accordance with the present invention, an orthotic 800 having attached thereto a forefoot post 810 mates to a toe extension portion 820 such that a continuous surface is provided between the front of the orthotic 800 and the toe extension 820. The toe extension 820 may be formed integrally with a forefoot post 810, or in some instances and depending upon the material from which the orthotic is made, may be formed integrally with the orthotic. Additionally, the toe extension 820 may be formed independently of the forefoot post, but configured with a tongue 830 to be inserted between the attachment devices of the post and the orthotic as shown in FIG. 6, as shown in FIG. 8B.

Figure 9A:
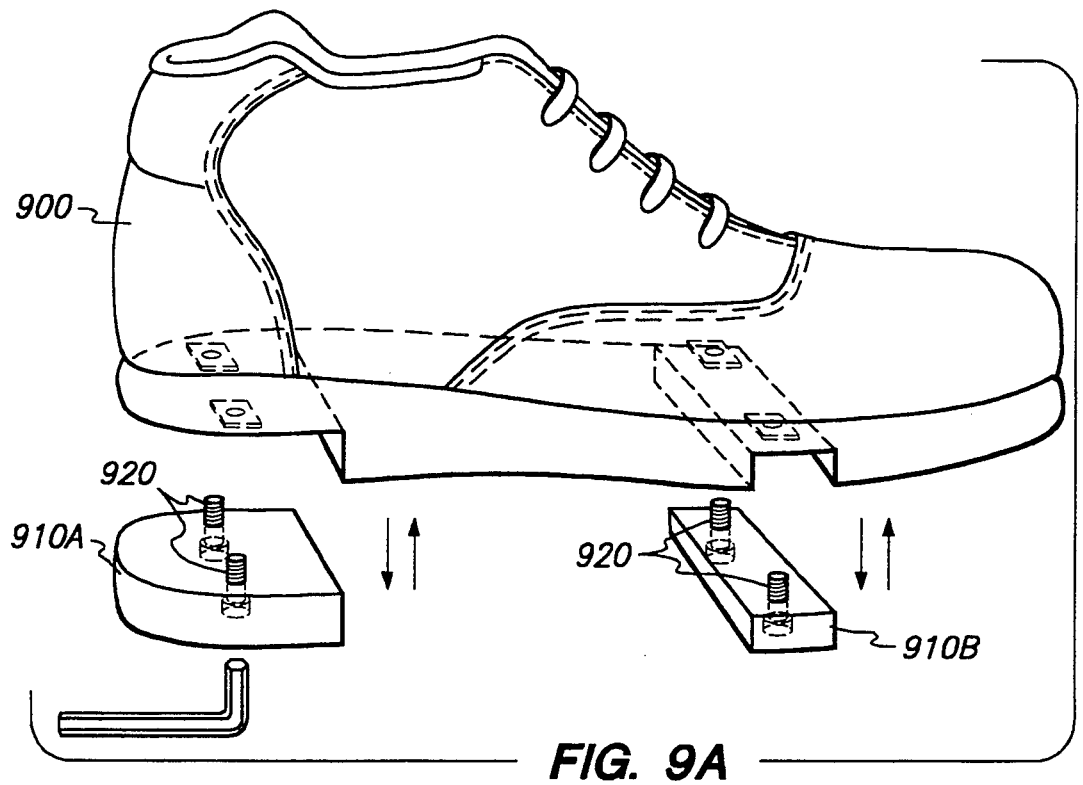
Figure 9B:
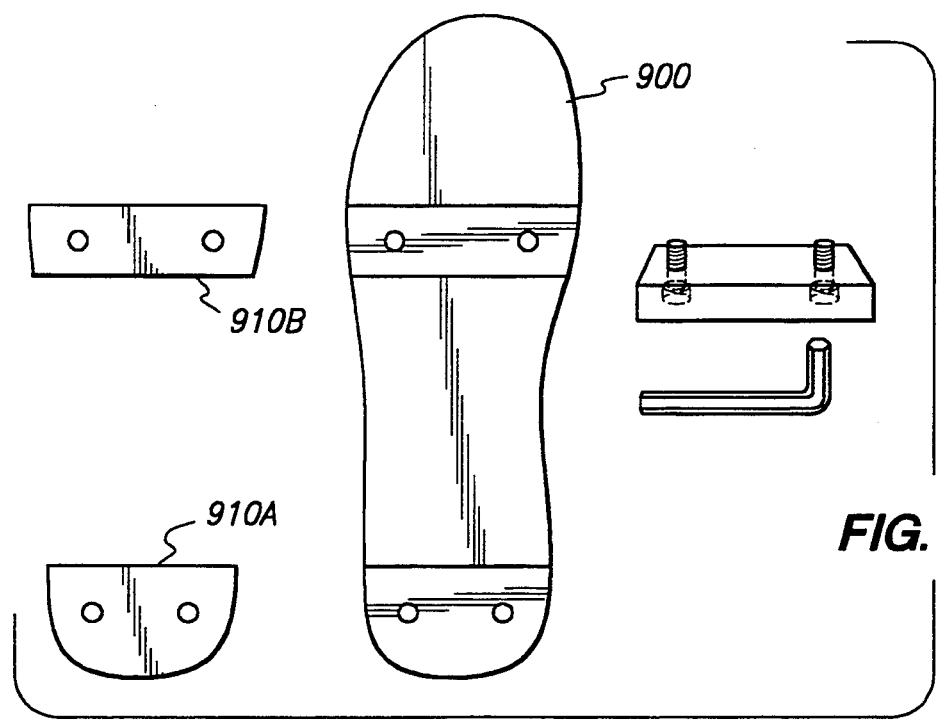
Figure 9C:
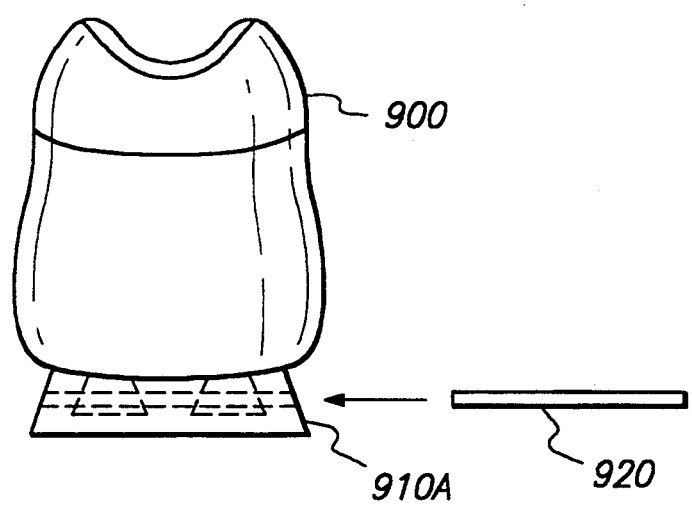
Figure 9D:
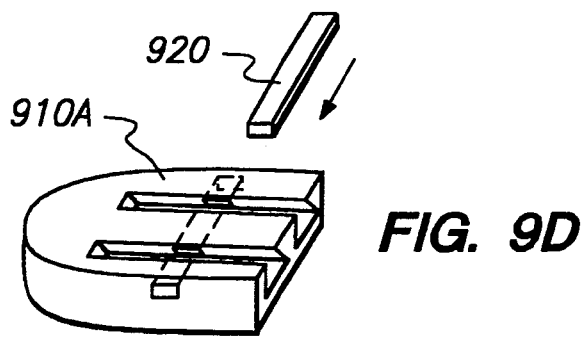
Figure 9E:
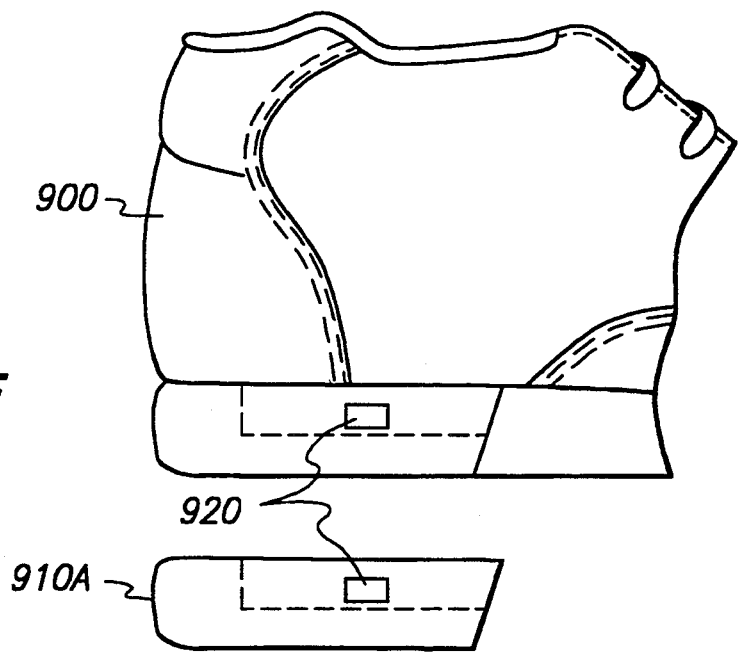

With reference next to FIGS. 9A–E, methods for attaching rearfoot and forefoot posts to a shoe using bolts or rods are shown. FIGS. 9A–B show from the right side and in partial cross-section view a shoe 900 of the type shown in FIG. 4, but wherein the posts 910A-B are affixed to the sole of the shoe by bolts or screws 920. Although Allen bolts are shown, any suitable screw or bolt is acceptable, or rods or mating geometries may be used as shown in FIGS. 9C–E.

Referring next to FIG. 10, another approach to affixing corrective posts to a shoe otherwise of the type shown in FIG. 4 may be appreciated. In the shoe 1000 shown in partial cross-sectional perspective view in FIG. 10, slots 1010A and 1010B are provided in the sole 1020, and posts 1030A and 1030B may be inserted into the slots 1010A-B, respectively. Due to the cross-sectional sizing of the posts 1030, the insertion of such posts causes a distortion of the sole of the foot appropriate to the required correction. While the posts 1030A and 1030B are sized sufficiently large that they wedge into place and should remain in place until intentionally removed, if additional security of attachment is desired a dowel or other device may be inserted into the sole 1020 and thence into the respective post 1030 to ensure that the respective post does not inadvertently work its way out of the slot.

Having fully described one embodiment of the present invention, it will be apparent to those of ordinary skill in the art that numerous alternatives and equivalents exist which do not depart from the invention set forth above. It is therefore to be understood that the invention is not to be limited by the foregoing description, but only by the appended claims.

What is claimed is:

1. An orthopedic corrective appliance kit for the feet comprising:

at least one footbed portion selectable by foot size for the right or the left foot and conforming substantially to right or left soles of the selected size, the at least one footbed portion formed from a material substantially non-deformable with respect to a ground surface;

a plurality of selectable wedge means defining different angles;

first attachment means beneath a rearfoot area of the at least one footbed portion for attaching at least one of the plurality of selectable wedge means; and second attachment means beneath a forefoot area of the at least one footbed portion for attaching at least one of the plurality of selectable wedge means, each of the plurality of selectable wedge means including mating connection means for interchangeably attaching to one of the first or second attachment means of the at least one footbed portion, the plurality of selectable wedge means enabling forefoot and rearfoot alignment of the feet while standing and walking to correct valgus and varus foot abnormalities.

2. The orthopedic kit of claim 1 wherein each of the first and second attachment means is at least one recess, and the mating connection means of each of the plurality of wedge means is at least one ridge for interchangeably mounting within the at least one recess of the at least one footbed portion.

3. The orthopedic kit of claim 1 wherein each of the first and second attachment means is a plurality of recesses and the mating connection means of the plurality of wedge means is a mating plurality of posts for interchangeably mounting with the plurality of recesses of the at least one footbed portion.

4. The orthopedic kit of claim 1 wherein each of the first and second attachment means is at least one recess and the mating connection means of the plurality of wedge means is at least one raised section having a mating, reversible geometry to the at least one recess in the at least one footbed portion.

5. The orthopedic kit of claim 1 wherein the plurality of wedge means comprises wedges defining at least three different angles for selectively changing the angle of the at least one footbed portion with respect to the ground surface.

6. The orthopedic kit of claim 1 further comprising arch support attachment means beneath an arch portion of the at least one footbed portion and removable arch support means defining means for connecting to the arch support attachment means.

7. The orthopedic kit of claim 1 wherein the at least one footbed portion is made from polyethylene terephthalate.

8. The orthopedic kit of claim 1 having a right and a left footbed portion, at least one of the plurality of selectable wedge means attachable, at either the first or second attachment means, to either the right or left footbed portions to correct valgus or varus foot abnormalities.

9. The orthopedic kit of claim 1 wherein the plurality of selectable wedge means comprises a first plurality of rearfoot wedge means for interchangeable connection to the first attachment means of the at least one footbed portion, and a second plurality of forefoot wedge means for interchangeable connection to the second attachment means of the at least one footbed portion.

10. The orthopedic kit of claim 9 wherein the first attachment means is at least one curved recess and each of the plurality of rearfoot wedge means defines a mating curved raised area for interchangeable attachment within the at least one curved recess of the at least one footbed portion, and where the second attachment means is at least one slot and each of the plurality of forefoot wedge means defines a mating raised area for interchangeable attachment within the at least one slot of the at least one footbed portion.

11. An orthopedic corrective appliance kit for the feet comprising:

a shoe having a sole;

a plurality of wedge means defining different angles;

first attachment means defined in a rearfoot area of the sole of the shoe for attaching at least one of the plurality of selectable wedge means; and second attachment means defined in a forefoot area of the sole of the shoe for attaching at least one of the plurality of selectable wedge means, the plurality of selectable wedge means defining mating connection means for interchangeably and reversible connecting to the first and second attachment means, the plurality of selectable wedge means enabling forefoot and rearfoot alignment of the foot to correct a majority of valgus foot abnormalities or varus foot abnormalities by substantially maintaining alignment of the feet while standing and walking.

12. The orthopedic corrective appliance kit of claim 11 wherein each of the first and second attachment means is at least one recess for receipt, from a right and a left side of the sole, of the least one wedge means to selectably correct for valgus and varus foot abnormalities.

13. The orthopedic corrective appliance kit of claim 11 wherein at least one of the wedge means is a heel of the shoe for connection to the first attachment means.

14. The orthopedic corrective appliance kit of claim 11 wherein the first attachment means is a threaded receiver and the second attachment means is a bolt member extending through at least a portion of at least one of the plurality of wedge means.

* * * * *